US00PP14658P29

(12) United States Plant Patent
Smith

(10) Patent No.: US PP14,658 P2
(45) Date of Patent: Mar. 30, 2004

(54) CHRYSANTHEMUM PLANT NAMED 'YOMARIAH'

(50) Latin Name: *Chrysanthemum×morifolium*
Varietal Denomination: Yomariah

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,546

(22) Filed: Mar. 25, 2003

(51) Int. Cl.[7] ..... A01H 5/00
(52) U.S. Cl. ..... Plt./286
(58) Field of Search ..... Plt./286, 295

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Yomariah', characterized by its upright, outwardly spreading and mounded plant habit; freely branching habit; uniform and freely flowering habit; daisy type inflorescences; golden yellow and orange-colored ray florets and bright yellow-colored disc florets; and natural season flowering in early October in the Northern Hemisphere.

1 Drawing Sheet

Botanical classification/cultivar designation: *Chrysanthemum×morifolium* cultivar Yomariah.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Yomariah'.

The new cultivar is a product of a planned breeding program conducted by the Inventor in Salinas, Calif. and Alva, Fla. The objective of the breeding program is to create new garden-type Chrysanthemum cultivars having inflorescences with desirable inflorescence forms, attractive floret colors and good garden performance.

The new Chrysanthemum originated from a cross made in September, 1998 in Salinas, Calif., of the *Chrysanthemum×morifolium* cultivar Donna, disclosed in U.S. Plant Pat. No. 7,512, as the female, or seed, parent with a proprietary seedling selection of *Chrysanthemum×morifolium* identified as code number 94-L258001, not patented, as the male, or pollen, parent. The new Chrysanthemum was discovered and selected by the Inventor as a single flowering plant within the progeny of the stated cross grown in a controlled environment in Alva, Fla. in November, 1999. The selection of this plant was based on its desirable inflorescence form, attractive ray floret color and good garden performance.

Asexual reproduction of the new cultivar by terminal cuttings taken in a controlled environment in Alva, Fla. since January, 2000, has shown that the unique features of this new Chrysanthemum are stable and reproduced true to type in successive generations.

SUMMARY OF THE INVENTION

The cultivar Yomariah has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomariah'. These characteristics in combination distinguish 'Yomariah' as a new and distinct cultivar:

1. Upright, outwardly spreading and mounded plant habit.
2. Freely branching habit; dense and full plants.
3. Uniform and freely flowering habit.
4. Daisy-type inflorescences with spoon-shaped ray florets.
5. Golden yellow and orange-colored ray florets and bright yellow-colored disc florets.
6. Natural season flowering in early October in the Northern Hemisphere.

In side-by-side comparisons conducted in Alva, Fla., plants of the new Chrysanthemum differed from plants of the female parent, the cultivar Donna, in the following characteristics:

1. Plants of the new Chrysanthemum flowered about two weeks later than plants of the cultivar Donna.
2. Plants of the new Chrysanthemum had smaller inflorescences than plants of the cultivar Donna.

In side-by-side comparisons conducted in Alva, Fla., plants of the new Chrysanthemum differed from plants of the male parent seedling selection, in the following characteristics:

1. Plants of the new Chrysanthemum flowered more uniformly, but about two weeks later than plants of the male parent seedling selection.
2. Plants of the new Chrysanthemum had daisy-type inflorescences with spoon-shaped ray florets whereas plants of the male parent seedling selection had duplex type inflorescences with elongated oblong-shaped ray florets.
3. Plants of the new Chrysanthemum and the male parent seedling selection differed in ray floret coloration as plants of the male parent seedling selection had purple-colored ray florets.

Plants of the new Chrysanthemum can also be compared to plants of the Chrysanthemum cultivar Oriole, disclosed in U.S. Plant Pat. No. 10,181. In side-by-side comparisons conducted in Alva, Fla., plants of the new Chrysanthemum differed from plants of the cultivar Oriole in the following characteristics:

1. Plants of the new Chrysanthemum were smaller and more rounded than plants of the cultivar Oriole.
2. Plants of the new Chrysanthemum flowered about three days earlier than plants of the cultivar Oriole.
3. Plants of the new Chrysanthemum had larger inflorescences than plants of the cultivar Oriole.
4. Ray florets of plants of the new Chrysanthemum were lighter in color than ray florets of plants of the cultivar Oriole.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yomariah'.

The photograph at the bottom of the sheet comprises a close-up view of typical inflorescences of the cultivar 'Yomariah'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Salinas, Calif., under natural season conditions and practices which approximate those generally used in commercial garden-type Chrysanthemum production. One cutting was planted in a 15.25-cm container in late May, 2002. Plants were not pinched, that is, the terminal apex was not removed to enhance branching. During the production of the plants, day temperatures averaged 20° C. and night averaged 13° C. Measurements and numerical values represent averages for typical flowering plants.

Botanical classification: *Chrysanthemum×morifolium* cultivar Yomariah.

Commercial classification: Daisy-type garden Chrysanthemum.

Parentage:

*Female, or seed, parent.*—*Chrysanthemum×morifolium* cultivar Donna, disclosed in U.S. Plant Pat. No. 7,512.

*Male, or pollen, parent.*—Proprietary seedling selection of *Chrysanthemum×morifolium* identified as code number 94-L258001, not patented.

Propagation:

*Type.*—Terminal tip cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Appearance.*—Perennial herbaceous daisy-type garden Chrysanthemum. Inverted triangle with rounded crown. Stems initially upright, then somewhat outwardly spreading giving a uniformly mounded appearance to the plant. Freely branching with lateral branches forming at every node.

*Plant height.*—About 23 cm.

*Plant diameter.*—About 46 cm.

*Lateral branches.*—Length: About 21.5 cm. Diameter: About 6 mm. Internode length: About 1.3 cm. Aspect: Upright and outwardly spreading. Texture: Pubescent. Color: 146A.

*Foliage description.*—Leaf arrangement: Alternate. Length: About 4.2 cm. Width: About 3.2 cm. Apex: Mucronate. Base: Attenuate. Margin: Palmately lobed, sinuses parallel to divergent. Texture, upper surface: Slightly pubescent. Texture, lower surface: Pubescent; veins prominent. Color: Developing and fully expanded foliage, upper surface: Darker than 147A. Developing and fully expanded foliage, lower surface: Darker than 147B. Venation, upper surface: 147A. Venation, lower surface: Close to 147B. Petiole length: About 1 cm. Petiole diameter: About 3 mm. Petiole color, upper surface: Close to 147B. Petiole color, lower surface: Close to 147B to 147C.

Inflorescene description:

*Appearance.*—Daisy-type inflorescence form with spoon-shaped ray florets. Inflorescences borne on terminals above foliage, arising from leaf axils. Disk and ray florets developing acropetally on a capitulum. About ten inflorescences per lateral.

*Flowering response.*—Under natural season conditions, plants flower in mid-October in the Northern Hemisphere.

*Inflorescence bud (before showing color).*—Height: About 4 mm. Diameter: About 6.5 mm. Shape: Oblate. Color (lower surface of phyllaries): Close to 147A.

*Inflorescence size.*—Diameter: About 4.9 cm. Depth (height): About 1.4 cm. Disc diameter: About 1.4 cm. Receptacle diameter: About 6 mm.

*Ray florets.*—Shape: Spoon-shaped. Length: About 2.4 cm. Corolla tube length: About 1.25 cm. Width: About 5 mm. Apex: Emarginate. Margin: Fused. Texture: Smooth, glabrous; satiny. Surface: Flat. Orientation: Initially upright, then perpendicular to vertical. Number of ray florets per inflorescence: About 52 in one or two whorls. Color: When opening and fully opened, upper surface: Close to 9A overlain with 46A to 53A; most densely overlain towards the apex. When opening and fully opened, lower surface: Close to 9C to 10A.

*Disc florets.*—Shape: Tubular; apex dentate, five-pointed. Length: About 5 mm. Width, apex: About 1.5 mm. Width, base: About 1 mm. Number of disc florets per inflorescence: About 107. Color: Immature: Close to 154D. Mature: Apex: 9A. Mid-section: Close to 146D. Base: Close to 155D.

*Peduncle.*—Strength: Strong. Aspect: About 45° from vertical. Length: First peduncle: About 4.5 cm. Fourth peduncle: About 6.5 cm. Seventh peduncle: About 8.75 cm. Diameter: About 2 mm. Texture: Pubescent. Color: 146A.

*Phyllaries.*—Quantity per inflorescence: About 23. Length: About 7 mm. Width: About 2 mm. Shape: Ligulate. Apex: Acute. Base: Truncate. Margin: Entire. Texture, upper surface: Smooth, waxy. Texture, lower surface: Pubescent. Color, upper and lower surfaces: Close to 147A.

*Reproductive organs.*—Androecium: Present on disc florets only. Anther color: 9A. Pollen: Scarce. Pollen color: 9A to 12A. Gynoecium: Present on both ray and disc florets.

*Seed/fruit.*—Seed and fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 37° C.

It is claimed:

1. A new and distinct cultivar of Chrysanthemum plant named 'Yomariah', as illustrated and described.

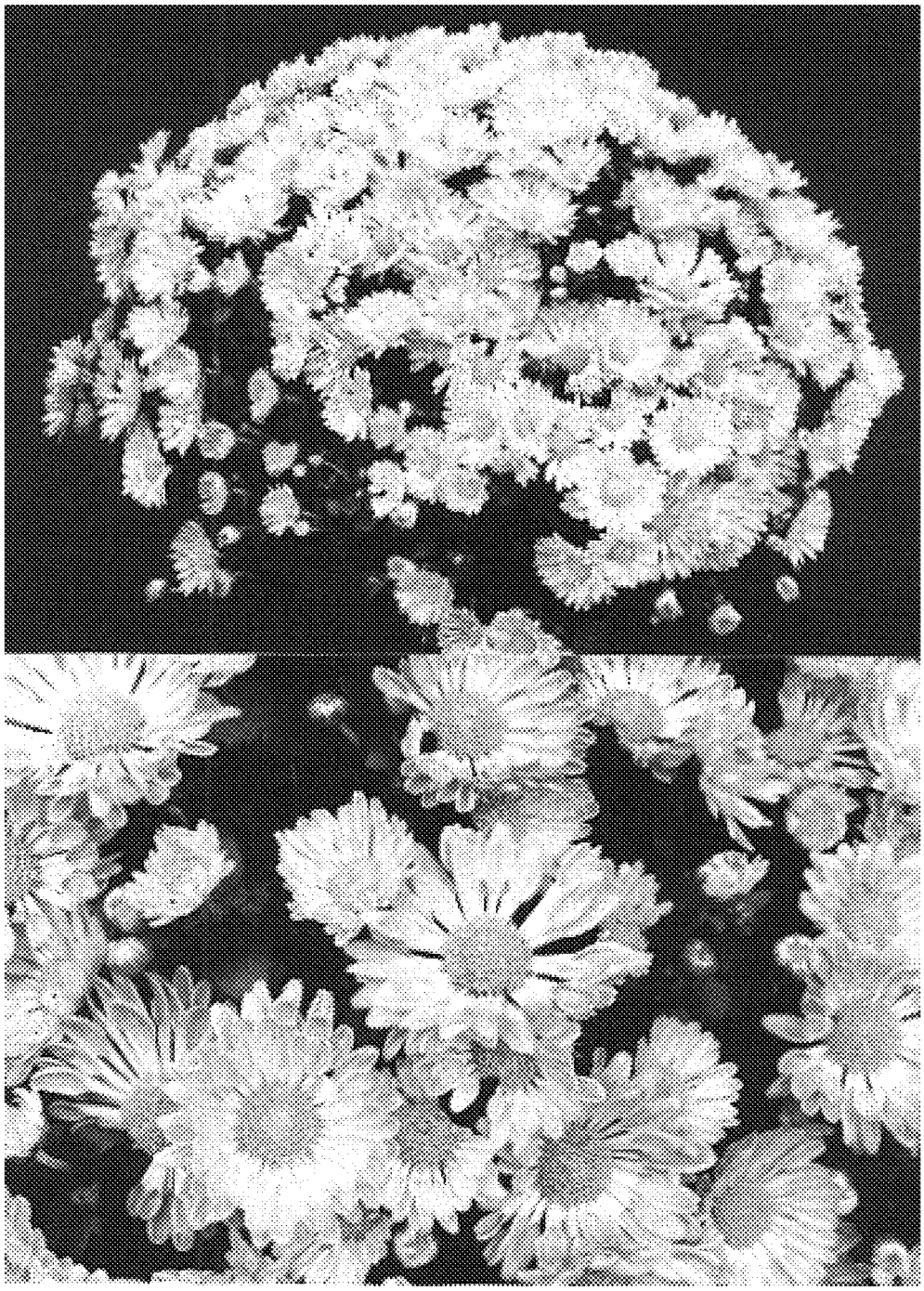

* * * * *